US00PP10606P

United States Patent [19]

Guillou et al.

[11] Patent Number: Plant 10,606

[45] Date of Patent: Sep. 15, 1998

[54] GERANIUM PLANT NAMED 'GUILAN'

[75] Inventors: Bernard Guillou; Jacques Guillou; Maurice Guillou, all of Saint-Malo, France

[73] Assignee: Guillou Freres J. B. et M., St. Malo, France

[21] Appl. No.: 724,510

[22] Filed: Sep. 30, 1996

[51] Int. Cl.[6] ..... A01H 5/00

[52] U.S. Cl. ..... Plt./87.12

[58] Field of Search ..... Plt./87.12

[56] References Cited

PUBLICATIONS

UPOV–ROM Plant Variety Database 1997–3. Pelargonium named 'Guilan' FR PBR 151125 title holder Guillou Freres.

*Primary Examiner*—James R. Feyrer

*Assistant Examiner*—Melissa L. Kimball

*Attorney, Agent, or Firm*—Foley & Lardner

[57] ABSTRACT

A new geranium plant named 'Guilan', characterized by single-type flowers with 5 petals per flower that are vividly carmine-pink in color; corolla diameter of 60 mm; early flowering which is luxuriant in the summer; plant habit that exhibits excellent branching with internode lengths of approximately 30 to 50 mm, plant height of approximately 120 to 150 cm, and ivy-shaped foliage lacking variegation but with distinctive green veins.

3 Drawing Sheets

1

The present invention comprises a new and distinct cultivar of geranium, botanically known as *Pelargonium peltatum* l'Hér. ex Ait., and hereinafter referred to by the cultivar name 'Guilan'. 'Guilan' is a product of planned breeding program which had the objective of creating new geranium varieties cultivars with a vivid pink flower color and compact and well-branched plant habit.

'Guilan' originated from a hybridization made in a controlled breeding program in Saint Malo, Bretagne, France, in 1988. The male and female parents were 'Duchesse Anne' and 'Corza', respectively. Both parents are from the proprietary 'Guillou' collection and are characterized by intense red color and double-type flowers. 'Guilan' was discovered and selected as one flowering plant within the progeny of the stated cross by the inventors in 1991 in a controlled environment in Saint Malo, France.

The first act of asexual reproduction, of 'Guilan' was accomplished when vegetative cuttings were taken from the initial selection in 1994 in a controlled environment in Haalderen, The Netherlands, by a technician working under the supervision of the inventors. Horticultural examination of selected units initiated in 1994 has demonstrated that the combination of characteristics as herein disclosed for 'Guilan' are firmly fixed and are retained through successive generations of asexual reproduction.

'Guilan' has not been observed under all possible environmental conditions. The phenotype may vary with variations in environment such as temperature, light intensity and daylength, without any change in genotype. The following observations, measurements, and comparisons describe plants grown in Haalderen, The Netherlands, under greenhouse conditions which approximate those generally used in commercial practice.

The following traits hae been repeatedly observed to be basic characteristics of 'Guilan' which in combination distinguish this geranium as a new and distinct cultivar:

1. Vivid pink single-type flowers.
2. Green-veined foliage.
3. Early flowering which is very luxuriant in the summer.

Of the many commercial cultivars known to the present inventors, 'Guilan' most closely resembles 'Corza' and 'Duchesse Anne' in plant habit.

2

The accompanying photographic drawings show typical flower and foliage characteristics of 'Guilan'.

Sheet 1 is a side view of a plant showing open and closed flowers.

Sheet 2 is a top and bottom view of an individual flower from the cultivar.

Sheet 3 is a top and bottom view of an individual leaf from 'Guilan'.

In the following description, color references are made to The Royal Horticultural Society (R.H.S.) Colour Chart. The color values were determined indoors in 1996 under greenhouse conditions at Haalderen, The Netherlands. Colors are as true as possible with illustrations of this type.

Classification:

*Botanical.*—cv., Guilan, *Pelargonium peltatum* l'Hér. ex Ait.

*Commercial.*—Ivy geranium designated 'Solo Single Pink'.

Inflorescence

A. Umbel:

*Average diameter.*—120 mm.

*Peduncle length.*—100 mm.

B. Corolla:

*Average diameter.*—60 mm.

*Form.*—Single type.

*Number of petals.*—5.

*Color (general tonality from a distance of three meters)* .—Carmine pink.

*Color (abaxial).*—Approx. R.H.S. 55A.

*Color (adaxial).*—Approx. R.H.S. 55C.

C. Bud:

*Shape.*—45 mm.

*Color (adaxial).*—Approx. R.H.S. 39A.

*Color (abaxial).*—Approx. R.H.S. 39A.

D. Reproductive organs:

*Androecium.*—Copious pollen.

*Gynoecium.*—Normally developed.

E. Spring flowering response period: 12–25 flowers opened 15 weeks after planting of unrooted cuttings (pinched plants).

F. Outdoor flower production: Outside culture is shorter than in greenhouse.

G. Durability: Excellent shatter resistance.

Plant

A. Foliage:

*Form.*—Ivy shaped.

*Margin.*—Dentated and veined; diameter (average 50–100 mm. wide and 30–60 mm wide).

*Color* (*abaxial*).—Light green.

*Color* (*adaxial*).—Light green.

*Color* (*zonation*).—Only adaxial/brown.

*Variegation.*—No.

*Margin.*—Indentations.

B. General appearance and form:

*Internode length.*—30–50 mm.

*Branching pattern.*—Excellent branching.

*Height.*—120–150 mm.

C. Tolerance to botrytis: Good resistance.

We claim:

1. A new and distinct cultivar of geranium plant named 'Guilan', as illustrated and described.

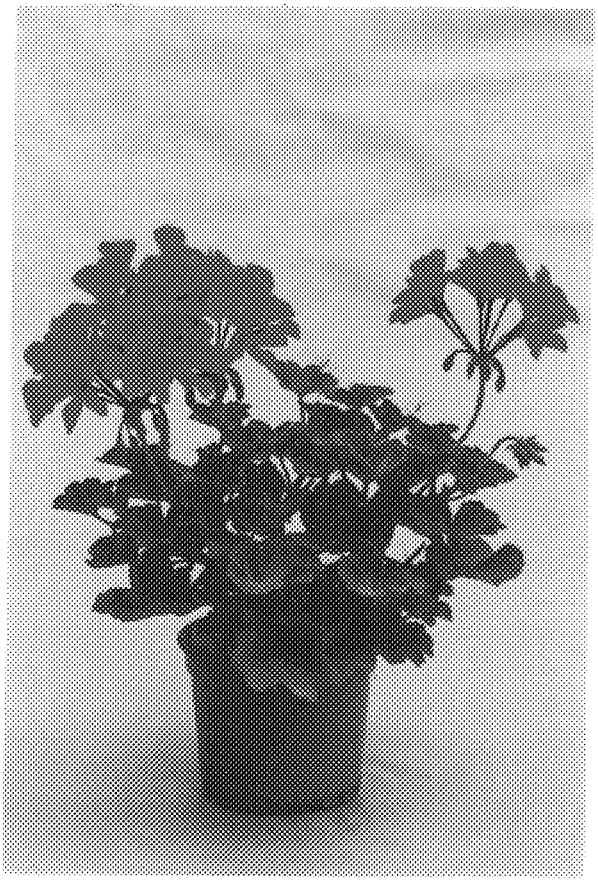

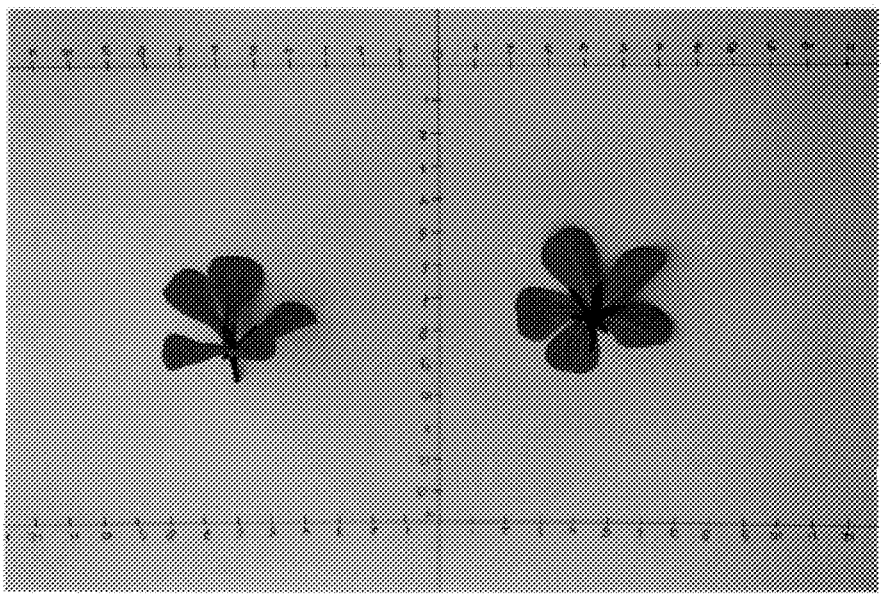

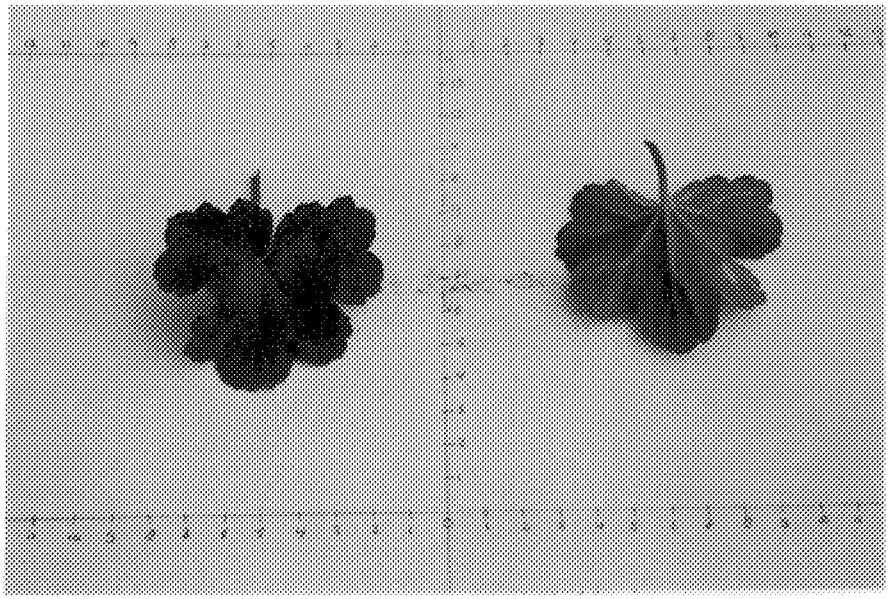

* * * * *